United States Patent
Rothmann et al.

(10) Patent No.: US 6,706,858 B2
(45) Date of Patent: Mar. 16, 2004

(54) USE OF ALKANES FOR CONTAMINATION-FREE PURIFICATION OR SEPARATION OF BIOPOLYMERS

(75) Inventors: Thomas Rothmann, Langenfeld (DE); Roland Fabis, Haan (DE); Andreas Schäfer, Leverkusen (DE); Sabine Dorit Menzel, Düsseldorf (DE); Thi My Chi Nguyen, Düsseldorf (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 10/277,767

(22) Filed: Oct. 22, 2002

(65) Prior Publication Data

US 2003/0100705 A1 May 29, 2003

Related U.S. Application Data

(63) Continuation-in-part of application No. 10/143,148, filed on May 10, 2002.

(51) Int. Cl.$^7$ .................................................. C08F 6/00
(52) U.S. Cl. ........................................ 528/491; 530/200
(58) Field of Search ........................ 528/491; 530/200

(56) References Cited

U.S. PATENT DOCUMENTS

| 4,329,448 A | * | 5/1982 | Cox et al. .................. 507/110 |
| 4,427,415 A | | 1/1984 | Cleveland |
| 4,777,021 A | | 10/1988 | Wertz et al. |
| 4,902,481 A | | 2/1990 | Clark et al. |

FOREIGN PATENT DOCUMENTS

| JP | 406062848 | * | 3/1994 |

* cited by examiner

*Primary Examiner*—Terressa M. Boykin
(74) *Attorney, Agent, or Firm*—Yankwich & Associates; Leon R. Yankwich; Michael R. Wesolowski

(57) ABSTRACT

The present invention relates to the use of alkanes for the contamination-free purification or separation of biopolymers.

23 Claims, No Drawings

USE OF ALKANES FOR CONTAMINATION-FREE PURIFICATION OR SEPARATION OF BIOPOLYMERS

This application is a continuation-in-part of U.S. application Ser. No. 10/143,148, filed May 10, 2002, claiming priority to German application 10122990.9, filed May 11, 2001.

FIELD OF THE INVENTION

The present invention relates to the use of hydrocarbons for preventing cross-contamination when eluting liquids from storage containers or sample containers, and a kit for this purpose. In particular, the present invention relates to the use of branched or unbranched hydrocarbons having 5–20 carbon atoms for the contamination-free separation and/or purification of biopolymers, particularly from liquids containing nucleic acids and proteins from plant, animal, or human cells or cell parts.

BACKGROUND OF THE INVENTION

In order to separate liquid samples into their individual components, purify specific components of the liquid sample, or filter the liquid samples, one normally places the liquid in (pipetted into) a sample container where it passes through a filter layer (filter paper, glass frit, membrane or material with selective absorption qualities) and passes, possibly drop wise, through an outlet opening into a collecting vessel arranged at a certain spacing underneath the sample container. The sample container and the collecting vessel are generally tubular in shape, with the filter layer resting on the base wall of the sample container, which is provided with the outlet opening. The outlet opening is a few tenths of a millimeter in diameter. A number of sample containers of this kind are arranged side by side in columns and rows and are connected to one another by means of a carrier plate. In particular, the liquid is forced through the filter layer by suction produced by a vacuum. For this purpose, a chamber that can be subjected to a vacuum is connected in an airtight manner to the carrier plate holding the sample containers. Inside the chamber are the collecting vessels associated with the sample containers, these collecting vessels being accommodated and held in a rack. Apparatus of this kind are used, for example, in technical and medical laboratories for simultaneously filtering a plurality of liquid samples from a number of patients.

Apparatus of this kind are known from U.S. Pat. Nos. 4,777,021 and 4,427,415. What both apparatus have in common is the fact the drops of sample liquid passing through the filter layers fall into a common tank-like collecting vessel that is part of the vacuum chamber, which is sealed off by the carrier plate connecting the individual sample containers together in a matrix arrangement. In the known apparatus for separating liquid samples, it is the components of the sample which are retained by, or in, the filter layer that are of interest in subsequent investigations. The liquid that passes through the filter layers is "lost" to further analysis. However, for separation in chemical or biopolymer preparation samples, it is essential that the sample ingredients passing through the filter layer, which have been washed or dissolved out of the filter layer by the application of solvents, be able to be collected individually or separately from one another.

U.S. Pat. No. 4,902,481 discloses an apparatus in which an insert having a plurality of collecting vessels arranged in a matrix is inserted in the vacuum chamber, the containers each being disposed underneath the sample containers. The carrier plate, which connects the sample containers with one another, is located at the upper ends of the sample containers. The sample containers, which are tubular in shape with their lower end closed off by the filter layer, are inserted in a holding plate with a plurality of openings that are provided on its upper surface with upright closed wheels. Adjoining each hole on the underside is a relatively short outlet tube with a stepped outer circumferential surface. Also formed on the underside of each outlet tube is a closed rim surrounding the tube, the diameter of these annular rims being identical to the diameters of the collecting vessels, which are arranged at a spacing below the closed rims on the underside of the holding plate. The outlet tubes do not extend into the associated collecting vessels.

The individual collecting vessels of the apparatus according to U.S. Pat. No. 4,902,481 are at only a short distance from one another. Because of the spacing of the collecting vessels from the sample containers, there is a risk that part of a drop of fluid that is to be collected by the collecting vessel arranged underneath a sample container will fall into an adjacent collecting vessel and contaminate the "filtrate" therein. Moreover, in the known apparatus according to U.S. Pat. No. 4,902,481, the drop formation is not uniform and, in particular, is irregular when the vacuum chamber is briefly ventilated in order to replace the set of collecting vessels housed therein with a new set. In fact, when the vacuum chamber is ventilated, the underside of the holding plate is wetted with fluid from the drops. When a vacuum is subsequently applied, relatively large drops are formed, as the wetness on the underside causes the liquid sucked-in to spread over the underside. The drop may reach as far as the annular rim, where it is sucked through the gap between the annular rim and the collecting vessel. Consequently, the liquid does not reach the desired collecting vessel but may, in some cases, enter an adjacent collecting vessel (contamination) or run over the outside of the collecting vessels. Contamination of the drops of liquid caught by the collecting vessels is unacceptable, particularly in the preparation of biopolymers from liquid samples, as this involves investigating nucleic acids and proteins after previously performing a number (25 to 40) of self-replicating cycles, e.g. in Polymerase Chain Reaction (PCR), where even slight contaminations (contaminations of 1:1000) will be multiplied and skew the results of the subsequent analysis.

The disadvantages described above cannot satisfactorily be overcome with the apparatus known in the prior art. In fact, it has been found that in the case of liquids or aqueous solutions such as buffer solutions that are sucked through the apparatus known from the prior art, e.g. by means of a vacuum, contamination cannot always be avoided.

If, for example, an elution buffer is sucked through a membrane by the application of a slight vacuum (residual pressure 800 mbar), then in up to 20% of cases a sizeable drop remains suspended from the outlet (nozzle) of the elution vessel. In the subsequent steps of the procedure there is thus a risk of the drop splashing into adjacent containers, which would involve undesirable cross-contamination.

If on the other hand the elution buffer is sucked out of the storage vessel by the application of a relatively high vacuum, then, as a rule, only a small drop remains on the outlet nozzle. The risk of the drop falling is thus reduced. On the other hand, with this type of elution, the risk of cross-contamination by aerosol formation is increased. In addition, numerous small drops collect on the walls of the collecting vessel, which are difficult to concentrate. As a result, the elution volumes are inconsistent in both elution methods.

The object of the present invention, therefore, is to allow elution to be carried out as completely as possible with reproducible elution volumes and to avoid the contamination of other samples with fluids for analysis.

SUMMARY

This object is achieved by the addition of branched or unbranched hydrocarbons to the aqueous mixtures to be analyzed, which contain the biopolymer or biopolymers as one component. These hydrocarbons may optionally carry substituents such as, for example, one or more halogen atoms, nitro groups or amino groups. The prerequisite for using substituted hydrocarbons is that they are immiscible with water. By biopolymers are meant, for the purposes of the present invention, naturally occurring macromolecules such as nucleic acids, proteins or polysaccharides, as well as synthetically produced polymers, e.g., those produced in fermentation processes, which contain the same or similar components to the natural macromolecules.

The word hydrocarbon for the purposes of the invention denotes primarily branched or unbranched, substituted or unsubstituted, acyclic or cyclic hydrocarbons having 5 to 20 carbon atoms. Branched or unbranched, substituted, acyclic or cyclic hydrocarbons having 6 to 16 carbon atoms are preferred.

Unsubstituted, acyclic, branched or unbranched hydrocarbons having 8 to 12 carbon atoms are particularly preferred, of which n-octane, n-nonane, n-decane and mineral oils are most preferred.

By mineral oils are meant, for the purposes of the present invention, the liquid distillation products obtained from mineral raw materials such as petroleum, lignites and mineral coals, wood or peat, which essentially consist of mixtures of saturated hydrocarbons [cf Römpp, Lexikon Chemie, Theime Verlag, Stuttgart].

Preferably, the amount of mineral oil/alkane solution added to the aqueous mixture to be analyzed correlates directly to the surface area of the filter to be used. Preferably, the ratio is in the range of 0.1 to 1.0$\mu$ of hydrocarbon solution per square millimeter (mm$^2$) of filter surface area.

DETAILED DESCRIPTION OF THE PREFERRED EMBODIMENT

The invention is further illustrated by the comparison examples that follow:

EXAMPLES

A Comparison Examples

The basic equipment for all the experiments that follow consists of a commercially obtainable Multiwell filtration plate (96-well filter plate having a filter diameter of 8 mm, such as the QIAplate made by QIAGEN GmbH, on which virus preparation has previously been carried out, or "unused status"). The following elution experiments were carried out:

1. Suction of 80 $\mu$l of elution buffer (water) under a pressure of 800 mbar over a period of 1 minute. The plate was then left to stand for a further 2 minutes. A marked formation of drops could then be observed on the underside of the plate.

Identical results were obtained with a buffer volume of 200 $\mu$l under a pressure of 800 mbar with a 2 minute elution period. When the experiments were carried out at a pressure of 500, 400 and 200 mbar, the walls of the collecting vessels (CTMs) were also wet with the fluid being analyzed.

2. Determining the elution volumes. 100 $\mu$l of water were sucked through a standard commercial filter plate (96 well, having a filter diameter of 8 mm) at a pressure of 800 mbar. The following volumes were obtained:

| | \multicolumn{12}{c}{100 $\mu$l} |
|---|---|---|---|---|---|---|---|---|---|---|---|---|
| | 1 | 2 | 3 | 4 | 5 | 6 | 7 | 8 | 9 | 10 | 11 | 12 |
| A | 65 | 60 | 74 | 58 | 53 | 73 | 55 | 62 | 73 | 55 | 65 | 100 |
| B | 67 | 58 | 60 | 77 | 74 | 75 | 75 | 75 | 70 | 70 | 65 | 100 |
| C | 70 | 58 | 60 | 70 | 75 | 73 | 60 | 63 | 72 | 70 | 68 | 90 |
| D | 60 | 65 | 60 | 58 | 75 | 60 | 65 | 63 | 72 | 64 | 70 | 92 |
| E | 75 | 58 | 60 | 74 | 75 | 60 | 73 | 63 | 53 | 55 | 72 | 100 |
| F | 65 | 74 | 73 | 77 | 75 | 60 | 73 | 60 | 72 | 75 | 72 | 95 |
| G | 75 | 74 | 75 | 58 | 59 | 60 | 73 | 75 | 60 | 72 | 72 | 85 |
| H | 75 | 74 | 75 | 58 | 75 | 60 | 75 | 57 | 72 | 75 | 62 | 86 |

MW 69.4
SD 10.2
Max. 100.0
Min. 53.0

Visual evaluation of the experiment indicated that there was a clear formation of droplets on the outlet openings. The elution volumes achieved were spread over a wide range.

B Examples According to the Invention

The experiments described in 1 (above) were repeated at a pressure of 200 mbar using 75 $\mu$l of water as the elution buffer and with the addition of 20 $\mu$l of n-octane, n-nonane, n-decane, and mineral oil solution.

There was no visible wetting of the inner walls of the collecting vessels with water droplets nor any formation of droplets on the plate or on the outlet openings in any of the cases.

In addition, uniform amounts of eluate were obtained, as demonstrated by the following comparison test:

| \multicolumn{4}{c}{Volume of Aqueous Eluate} | | | |
|---|---|---|---|
| add 90 $\mu$l without oil | | add 85 $\mu$l plus 30 $\mu$l oil | |
| 67 | 66 | 69 | 69.5 |
| 54 | 65 | 70 | 70 |
| 65 | 63 | 69 | 71 |
| 67 | 63 | 70 | 70 |
| 30 | 55 | 70 | 67 |
| 32 | 30 | 70 | 70 |
| 30 | 30 | 65 | 70 |
| 64 | 50 | 68 | 74 |

MW ($\mu$l)        MW ($\mu$l)
51.9               69.5
SD                 SD
15.8               1.9

The results of this comparison were as follows:

1. Larger droplets of eluate were suspended from the nozzle for elution without oil. To some extent the drops were pulled away as the plate was removed (cross-contamination).

2. For elution with oil, a thin film of oil was suspended from the nozzles. The film of oil remained on the nozzle.

3. The volume of eluate for elution with oil was 20 $\mu$l greater.

4. For the elution with oil, the volume of eluate was more uniform (SD 1.9 versus 15.8).

What is claimed is:

1. A method for separating biopolymers from an aqueous solution comprising (a) mixing an aqueous solution containing a biopolymer of interest with at least one hydrocarbon and (b) separating said biopolymer from other components of said solution by filtration.

2. The method of claim 1, wherein said separation step (b) employs vacuum filtration.

3. The method of claim 1, wherein the biopolymer is collected in the filtrate.

4. The method of claim 1, wherein the hydrocarbon is an unsubstituted alkane.

5. The method of claim 1, wherein the hydrocarbon is a substituted water-immiscible alkane.

6. The method of claim 1, wherein the hydrocarbon is an acyclic alkane.

7. The method of claim 1, wherein the hydrocarbon is an unbranched acyclic alkane.

8. The method of claim 1, wherein the hydrocarbon is a branched acyclic alkane.

9. The method of claim 1, wherein the hydrocarbon is a cyclic alkane.

10. The method of claim 1, wherein the hydrocarbon is an alkane having 5 to 20 carbon atoms.

11. The method of claim 1, wherein the hydrocarbon is an alkane having 6 to 16 carbon atoms.

12. The method of claim 1, wherein the hydrocarbon is an alkane having 8 to 12 carbon atoms.

13. The method of claim 1, wherein the hydrocarbon is selected from the group of n-octane, n-nonane, n-decane, and n-dodecane.

14. The method of claim 1, wherein the hydrocarbon is a mixture of two or more alkanes (mineral oil).

15. The method of claim 1, wherein 0.1 to 1.0 microliters of said hydrocarbon is added per square millimeter of a filter surface area.

16. In a method of separating a biopolymer from an aqueous mixture by filtration, the improvement comprising adding a hydrocarbon to the mixture prior to elution of the biopolymer.

17. The improvement of claim 16, wherein said hydrocarbon is an alkane of 5–20 carbon atoms.

18. The improvement of claim 17, wherein said alkane is selected from the group of n-octane, n-nonane, n-decane, n-dodecane, and mixtures thereof.

19. The improvement of claim 17, wherein 0.1 to 1.0 microliters of said alkane is added per square millimeter of a filter surface area.

20. A kit for the purification or separation of biopolymers, comprising a container of at least one hydrocarbon and instructions for carrying out the method according to claim 1.

21. The kit of claim 20, wherein said hydrocarbon is an alkane of 5–20 carbon atoms.

22. The kit of claim 21, wherein said alkane is selected from n-octane, n-nonane, n-decane, n-dodecane, and mixtures thereof.

23. The kit of claim 22, wherein 0.1 to 1.0 microliters of said alkane is added per square millimeter of a filter surface area.

* * * * *